Dec. 21, 1954 F. C. CHANDLER Plant Pat. 1,332
ROSE RED VERBENA PLANT
Filed March 12, 1954
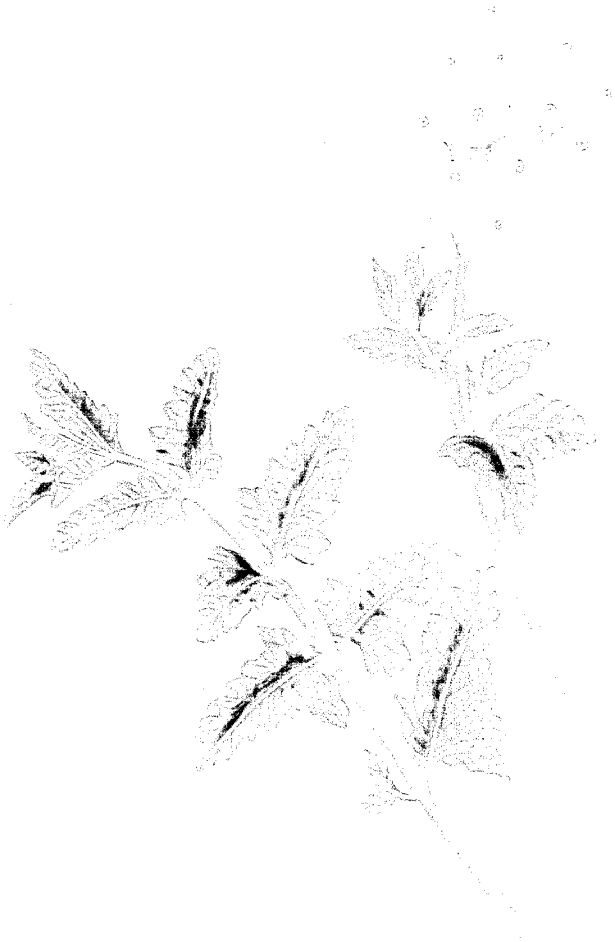
INVENTOR.
Florence Clyde Chandler
BY
Pennie, Edmonds, Morton, Barrows & Taylor
ATTORNEYS United States Patent Office Plant Pat. 1,332
Patented Dec. 21, 1954

1,332

ROSE RED VERBENA PLANT

Florence Clyde Chandler, Ardsley, N. Y., assignor to Boyce Thompson Institute for Plant Research, Inc., Yonkers, N. Y., a corporation of New York Application March 12, 1954, Serial No. 415,994

1 Claim. (Cl. 47—60)

This invention provides a new and distinct variety of rose red verbena plant. The new variety of plant is particularly characterized by its unique rose red flowers which are large forming medium large clusters of many flowers which are borne on long, stiff stems, by its large thick, medium green leaves, by erect habit, and by good vigor. The new variety has been reproduced asexually from cuttings and the characteristics appear to be fixed.

A diploid seedling from a bed of mixed verbenas was selected for its rose color and was propagated vegetatively. Cuttings from these actively growing plants were treated with colchine resulting in a plant which is a tetraploid with $2n=20$ chromosomes. This tetraploid was crossed with a spectrum red verbena diploid with $2n=10$ chromosomes of the type now in cultivation. This crossing resulted in the verbena triploid rose red with $2n=15$ chromosomes. The new variety of plants, as thus originated, were asexually reproduced from cuttings at Boyce Thompson Institute for Plant Research, Inc., Yonkers, New York.

In the accompanying drawing a plant of the invention is illustrated by a painting of a mature plant in substantially full bloom.

*Flowers*

The bright rose red color of the flowers is distinct from all other verbena flowers. According to Ridgway's "Color Standards and Nomenclature," published by the author from the press of A. Hoen and Company, the color is nearest rose red. According to Munsell "Book of Color," published by Munsell Color Company, Inc., Baltimore, Md., the flowers are uniformly R 4/14 (red hue, 4 value, 14 chroma). The individual flowers are about one inch in diameter and an average of about 30 flowers form clusters which measure about 2½ inches in diameter and about 2 inches in axial length. The young flowers have a small white eye which is not so pronounced in the older flowers. The individual stems are nearly ⅛ inch in diameter, usually 16 inches in length, and stems with several flower clusters measure as much as 23 inches in length. The flower clusters are usually from 15 to 16 inches above the ground.

*Leaves*

The leaves are thick and medium green and are generally about 1½ inches in diameter and about 2 inches in length near the base, while the leaves at the tips of the branches are smaller.

*Seeds*

No seeds have been obtained to controlled self-pollinations, and the plant is propagated only by vegatative cuttings. The pollen is about 38% aborted and the grains are from 47.5 to 62 microns in diameter.

*General*

The plant is generally erect, its vegetative habit is good, and it is more vigorous than the usual spectrum red verbena. The plant remains in good vegetative condition throughout the summer and the leaves remain green and do not burn during the summer. The plant flowers well and has a profusion of bloom throughout the summer and until killed by frost.

I claim:

The new and distinct variety of rose red verbena plant substantially as illustrated and described, characterized by very large individual flowers of bright rose red color in large clusters of many flowers borne on stiff, long stems, by large, thick and medium green leaves, and by good vigor.

No references cited.